US006562582B2

(12) United States Patent
Mitchell et al.

(10) Patent No.: US 6,562,582 B2
(45) **Date of Patent: *May 13, 2003**

(54) CHLAMYDIA-FREE CELL LINES AND ANIMALS

(75) Inventors: William M. Mitchell, Nashville, TN (US); Charles W. Stratton, Nashville, TN (US)

(73) Assignee: Vanderbilt University, Nashville, TN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/025,174

(22) Filed: Feb. 18, 1998

(65) Prior Publication Data

US 2002/0009802 A1 Jan. 24, 2002

Related U.S. Application Data

(63) Continuation of application No. 08/911,593, filed on Aug. 14, 1997, now abandoned.

(60) Provisional application No. 60/023,921, filed on Aug. 14, 1996.

(51) Int. Cl.[7] .......................... C12Q 1/18; C12Q 1/22; A61K 49/00

(52) U.S. Cl. .......................... 435/32; 435/31; 435/325; 435/366; 424/9.1; 424/405; 800/2

(58) Field of Search .......................... 424/405, 9.1, 114, 424/116; 435/31, 32, 325, 366; 800/2

(56) References Cited

U.S. PATENT DOCUMENTS

| | | | | |
|---|---|---|---|---|
| 5,000,958 A | * | 3/1991 | Fountain et al. | 424/450 |
| 5,232,829 A | * | 8/1993 | Longiaru et al. | 435/6 |
| 5,612,473 A | * | 3/1997 | Wu et al. | 536/25.42 |
| 5,741,525 A | * | 4/1998 | Larsen | 424/616 |
| 5,773,234 A | * | 6/1998 | Pronovost et al. | 435/7.36 |
| 5,888,973 A | * | 3/1999 | Lambert, Jr. | 514/12 |

OTHER PUBLICATIONS

Claas et al. J. Clin. Microbiol. vol. 29 (1), pp. 42–45, Jan. 1991.*

Mahony et al. J. Clin. Microbiol. vol. 30 (9), pp. 2241–2245, Sep. 1992.*

Lanham et al. J. Rheumatol. vol. 23 (3), pp. 225–226, abstract enclosed, 1984.*

Jones et al. Rev. Infect. Dis. vol. 5, Suppl. 3, pp. S556–S561, Jul. 1983.*

Dean et al. J. Infectious Dis. vol. 166, pp. 383–392, Aug. 1992.*

Ripa et al. J. Clin. Microbiol. vol. 6 (4), pp. 328–331, 1977.*

Heinonen, Pentti K., et al., "A Comparison of Ciprofloxacin with Doxycycline plus Metronidazole in the Treatment of Acute Pelvic Inflammatory Disease", *Scand. J. Infect. Dis. Suppl.*, 60: 66–73.

Burchell, H.J., et al., "Efficacy of Different Antibiotics in the Treatment of Pelvic Inflammatory Disease", *SAMJ.*, 72: 248–249 (Aug. 15, 1987).

Paavonen, J., et al., "Factors Predicting Abnormal Hysterosal–pingographic Findings in Patients Treated for Acute Pelvic Inflammatory Disease", *Int. J. Gynaecol. Obstet.*, 23: 171–175 (1985).

Miettinen, A., et al., "The Effect of Ciprofloxacin and Doxycycline Plus Metronidazole on Lower Genital Tract Flora in Patients with Proven Pelvic Inflammatory Disease", *Arch. Gynecol. Obstet.*, 249: 95–101 (1991).

Judlin, P., et al., "Etude Comparative Des Associations Ofloxacine+Amoxicilline–Acide Clavulanique Versus Doxycycline+Amoxicilline–Acide Clavulanique Dans Le Traitement Des Infections Génitales Hautes A *Chlamydia Trachomatis", J. Gynecol. Obstet. Biol. Reprod.*, 24: 253–259 (1995).

Henry–Suchet, J., "Traitement Des Infections Utéro–Annexielles Sexuellement Transmises (IUAST) Sauf Syphilis Et Herpès", *Méd. Mal. Infect.*, 24: 379–387 (1994).

Joly–Guillou, M.L., et al., "Bactéries Isolées En 1994–1995 Au Cours Des Infections Gynécologiques Hautes Et Des Uréthrites Masculines", *La Presse Médicale 2–9 Mars 25*, (8): 342–348.

Orfila, J. and Haider, F., "Comparative Study Of The In Vitro Activity Of Lomefloxacin Versus Lomefloxacin Combined With Metronidazole Versus Lomefloxacin In Combination With Amoxicillin/Clavulanic Acid Against *Chlamydia trachomatis", Intern. J. Antimicro. Agents*, 2: 11–14 (1992).

Witte, E.H., et al., "A Comparison Of Pefloxacin/Metronidazole And Doxycycline/Metronidazole in the Treatment of Laparoscopically Confirmed Acute Pelvic Inflammatory Disease", *Eur. J. Obstet. Gynec. and Repro. Bio.*, 50: 153–158 (1993).

* cited by examiner

*Primary Examiner*—Christopher R. Tate
(74) *Attorney, Agent, or Firm*—Clark & Elbing LLP

(57) ABSTRACT

Methods for clearing Chlamydia from biological materials, e.g., cells and animals, infected therewith are described. Methods for maintaining Chlamydia-free cells and animals are also described.

24 Claims, No Drawings

CHLAMYDIA-FREE CELL LINES AND ANIMALS

RELATED APPLICATION

This application is a continuation of U.S. Ser. No. 08/911,593, filed Aug. 14, 1997 (now abandoned), which claims benefit from U.S. Ser. No. 60/023,921 filed Aug. 14, 1996 (now abandoned).

BACKGROUND OF THE INVENTION

Chlamydiae are obligate intracellular microorganisms which parasitize eukaryotic cells and are ubiquitous throughout the animal kingdom. Members of the chlamydial genus are considered bacteria with a unique biphasic developmental cycle having distinct morphological and functional forms. This developmental growth cycle alternates between 1) intracellular life forms, of which two are currently recognized, a metabolically-active, replicating organism known as the reticulate body (RB) and a persistent, non-replicating organism known as the cryptic phase; and 2) an extracellular life form that is an infectious, metabolically-inactive form known as the elementary body (EB).

EBs are small (300–400 nm) infectious, spore-like forms which are metabolically inactive, non-replicating, and found most often in the acellular milieu. EBs are resistant to a variety of physical insults such as enzyme degradation, sonication and osmotic pressure. This physical stability is thought to be a result of extensive disulfide cross-linking of the cysteine-rich major outer membrane protein (MOMP) (Bavoil et al., *Infection and Immunity,* 44:479–485 (1984); Hackstadt et al., *Journal of Bacteriology,* 161:25–31 (1985); Hatch et al., *Journal of Bacteriology,* 165:379–385 (1986); Peeling et al., *Infection and Immunity,* 57:3338–3344 (1989); J. C. A. Bardwell, *Molecular Microbiology,* 14:199–205 (1994); and T. P. Hatch, *Journal of Bacteriology,* 178:1–5 (1993)). Under oxidizing conditions in the acellular milieu of the host, the outer membrane of EBs is relatively impermeable as well as resistant to inactivation. EBs are thus well suited to survive long enough outside of their hosts to be transmitted to a new host in the form of a droplet nuclei (Theunissen et al., *Applied Environmental Microbiology,* 59:2589–2593 (1993)) or a fomite (Fasley et al., *The Journal of Infectious Diseases,* 168:493–496 (1993)).

Once fully established, the Chlamydia are difficult to eradicate, with frequent relapse following antibiotic therapy. Evidence also indicates that the Chlamydia may become dormant and are then shed in quantities too few to reliably detect by culture.

*C. pneumoniae* is the most recent addition to the genus Chlamydiae and is well-accepted as a human pathogen that is difficult to eradicate by standard antibiotic therapy (Hammerschlag et al., *Clin. Infect. Dis.* 14:178–182 (1992)). *C. pneumoniae* is known to persist as a silent or mildly symptomatic pathogen, resulting in a chronic, persistent infection (Schacter, J., In: *Baun AL*, eg. *Microbiology of Chlamydia*, Boca Raton, Fla., CRC Press, 1988, pp. 153–165).

The current therapy for suspected/confirmed *C. pneumoniae* infection is with a short course (e.g., 2–3 weeks) of a single antibiotic. *C. pneumoniae* is susceptible in vitro to tetracyline, erythromycin, clarithromycin, and fluoroquinolones such as ofloxacin and sparfloxacin (Kuo et al., *Antimicrob. Agents Chemother.,* 32:257–258 (1988); Welsh et al., *Antimicrob. Agents Chemother.,* 36:291–294 (1992); Chirgwin et al., *Antimicrob. Agents Chemother.,* 33:1634–1635 (1989); Hammerschlag et al., *Antimicrob. Agents Chemother.,* 36:682–683 (1992); Hammerschlag et al., *Antimicrob. Agents Chemother.,* 36:1573–1574); M. R. Hammerschlag, *Antimicrob Agents Chemother.,* 38:1873–1878 (1994); M. R. Hammerschlag, *Infect. Med.,* 64–71 (1994)). Despite this demonstration of in vitro susceptibility, *C. pneumoniae* infections may relapse following antibiotic therapy with these agents. In vitro studies on the persistence of Chlamydiae despite specific and appropriate antibiotic therapy have suggested that the presence of antibiotics promotes the formation of an intracellular, non-replicative state (Beatty et al., *Microbiol. Rev.* 58:686–699 (1994)), typically referred to as the latent or cryptic phase. This change can be thought of as a stringent response and is seen also with nutrient starvation and exposure to gamma-interferon. Removal of the stressful influence allows the organism to resume replication. Thus, in this way, the organism can escape current antibiotic therapy used in clinical practice.

In view of the chronic and persistent nature of chlamydial infections, there is a need for reliable, accurate methods for diagnosis of pathogenic infection as well as therapeutic approaches to manage the infection. Due to the highly infective nature of Chlamydia EBs and their ability to reinfect cells, there is also a need for antichlamydial therapy which totally eradicates this pathogen, including the non-replicating cryptic phase and the extracellular phase, as well as the replicating reticulate body (RB). Eradication of all phases of the organism from the host will prevent the long term sequelae of such chronic infections such as coronary artery atheromatosis and other idopathic inflammatory diseases, recognized now as being associated with *C. pneumoniae* infection.

Because they are intracellular parasites, micro-organisms such as the chlamydiae cannot be cultured without the use of animal or tissue cultures. Continuous cell lines routinely used to cultivate *C. pneumoniae* include HL, Hep2, HeLa, H-292, HuEVEC and McCoy cells; stocks can be obtained from a commercial supplier (e.g., Bartells), from the American Type Culture Collection (ATCC), or from The Washington Research Foundation in the case of HL cells.

SUMMARY OF THE INVENTION

The present invention pertains to methods for clearing biological material infected with Chlamydia to produce Chlamydia-free cell lines and animals, and to methods of maintaining biological material, e.g., cell lines and animals, such that they remain Chlamydia-free. According to the method, a biological material is cleared from Chlamydia infection by contacting the biological material with at least two agents, each of which is effective against a different phase of the chlamydial life cycle, until the biological material no longer tests positive for Chlamydia. The agents can be selected from the group consisting of a) agents effective against the cryptic phase of the chlamydial life cycle; b) agents effective against the elementary body phase of the chlamydial life cycle; and c) agents effective against the replicating phase of the chlamydial life cycle. In one embodiment, the agent effective against the elementary body phase is a disulfide reducing agent. In another embodiment, the agent effective against the cryptic phase is a nitroaromatic compound, such as nitroimidazoles, nitrofluans, analogs, derivatives and combinations thereof.

Biological material that has been cleared of Chlamydia infection, according to the methods of this invention, are also described. The biological material can be a continuous cell line such as HeLa-CF, HL-CF, H-292-CF, HuEVEC-CF and McCoy-CF; wherein "CF" is a shorthand annotation for "Chlamydia-free". Alternatively, the biological material can be an animal, such as a mouse, rabbit or other animal model, which is negative for Chlamydia.

The invention also pertains to methods of maintaining a Chlamydia-free status in animals and cell lines which have been cleared of Chlamydia infection by the methods of this invention, or have never been infected, such as their Chlamydia-free offspring or progeny. Cells or animals can be maintained as Chlamydia-free by maintaining them on antibiotics and/or treating their nutrients and environment to ensure that they are Chlamydia-free. Particularly, a source of nutrients to be administered to Chlamydia-free cells or animals can be treated to inactivate or remove any chlamydial elementary bodies therefrom. This can be accomplished by exposing the nutrients to gamma irradiation for a period of time and level of exposure adequate to inactivate the elementary bodies. In addition to, or alternatively, a source of nutrients can be passed through a filtration system to physically remove the chlamydial elementary bodies therefrom. Optionally, the source of nutrients can be first treated with a disulfide reducing agent, such as dithiothreitol, before the filtration step is performed. The filter should be of adequate size such that objects larger than 0.5 microns are prevented from passing through.

The invention further pertains to a diagnostic kit or pack comprising an assembly of materials selected from the group consisting of antibiotics, reagents, Chlamydia-free cell lines, and combinations thereof, or other materials that would be necessary to perform any of the methods described herein.

DETAILED DESCRIPTION OF THE INVENTION

The present invention provides a unique approach for creating and maintaining animals and cell lines which are free of Chlamydia infection. Also described herein are methods for creating nutrients and culture media that are suitable for use with animals and cell lines that have been cleared of Chlamydia infection.

Attempts to culture isolates of *C. pneumoniae* from blood and cerebrospinal fluid (CSF) have resulted in the discovery that the continuous cell lines routinely used to cultivate *C. pneumoniae* are cryptically infected with *C. pneumoniae*. These include not only in house stocks of HeLa, HL, H-292, HuEVEC and McCoy cells, but also stocks obtained from the American Type Culture Collection (ATCC), The University of Washington Rearch Foundation for HL cells, as well as a commercial supplier (Bartells) of H-292 and McCoy cells for the clinical culture of Chlamydia. The presence of a cryptic form of *C. pneumoniae* in these cells has been repeatedly demonstrated by solution PCR amplifying the MOMP. In situ PCR in HeLa cells against the MOMP demonstrates the MOMP genes to be present in 100% of cells. Nevertheless, fluoroscenated mAb to LPS in McCoy cells does not yield any indication of Chlamydia (i.e., reactive against all Chlamydia) while fluoroscenated mAb to *C. pneumoniae* MOMP yields a generalized fluorescence throughout the cytoplasm that can be confused with nonspecific autofluorescence. Infection with Chlamydia trachomatis (Bartells supply) yields the typical inclusion body staining with the LPS mAb (i.e., cross reactive with all species of Chlamydia) with no change in cytoplasmic signal with anti-MOMP mAb against *C. pneumoniae.* These findings (solution PCR, in situ PCR, mAb reactivity) were interpreted as consistent with a cryptic (non-replicating) infection by *C. pneumoniae* of cells commonly used to culture the organism. Further, virtually all rabbits and mice tested to date have PCR signals for the *C. pneumoniae* MOMP gene.

This creates a currently unrecognized problem of major significance for those clinical labs providing *C. pneumoniae* culture services as well as investigators who now do not know whether their results in animals or in cell culture will be affected by cryptic chlamydial contamination. Clinical and research laboratories currently have no way to determine whether an organism is, in fact, Chlamydia-free.

This invention pertains to a method for clearing cells and animals of *C. pneumoniae* and keeping them clear. Clearing them entails contacting the infected organism with agents used singly or in combination to eliminate or interfere with more than one of the distinct phases of the life cycle of Chlamydia species. Keeping them clear entails either maintaining them on antibiotics and/or treating their nutrients and environment to ensure they are Chlamydia-free. In a preferred embodiment, maintenance conditions comprise a combination of isoniazid (INH) (1 $\mu$g/ml), metronidazole (1 $\mu$g/ml), and dithiothreitol (10 $\mu$M) in the culture medium. Media changes are accomplished every 3 days or twice per week. The cells can be removed from the protective solution between 1 and 7 days before they are to be used for culture or other purpose.

These techniques have now made it possible to create a variety of Chlamydia-free (CF) organisms, including continuous cell lines called HeLa-CF, HL-CF, H-292-CF, HuEVEC-CF, McCoy-CF, African green monkey and other cell lines that are capable of supporting chlamydial growth. Various CF strains of mice, rabbits and other animal models for research use can be produced. These Chlamydia-free organisms can be used as diagnostic tools for the methods described below and in U.S. patent application Ser. No. 08/911,593 filed Aug. 14, 1997, entitled "Diagnosis and Management of Infection Caused by Chlamydia" by William M. Mitchell and Charles W. Stratton; and U.S. patent application Ser. No. 09/025,521, entitled "Diagnosis and Management of Infection Caused by Chlamydia", filed Feb. 18, 1998; the entire teachings of which are incorporated herein by reference.

Diagnosis of Chlamydia Infection

The presence of Chlamydia in a biological material can be determined using the techniques described herein such as, but not limited to, immunofluorescence assay, tagged-antibody assays, an immunohistochemical staining assay, an immunometalic electronic microscopy assay, and in situ or solution DNA amplification assays. For purposes of this application, "biological material" includes, but is not limited to, bodily secretions, bodily fluids and tissue specimens. Examples of bodily secretions include cervical secretions, trachial-bronchial secretions and pharyngeal secretions. Suitable bodily fluids include blood, sweat, tears, cerebral spinal system fluid, serum, urine, snyovial fluid and saliva. Animals, cells and tissue specimens such as from a variety of biopsies are embraced by this term.

The methods of this invention entail using any known techniques for nucleic acid (e.g., DNA and RNA) amplification. Preferred amplification techniques are the polymerase chain reaction (PCR) methodologies which comprise solution PCR and in situ PCR, to detect the presence or absence of unique genes of Chlamydia. Species-specific assays for detecting Chlamydia can be designed based upon the primers selected.

In general, solution PCR is carried out on a biological material by first pre-incubating the material in an appropriate reducing agent that is capable of reducing the disulfide bonds which maintain the integrity of the MOMP and other surface proteins of the chlamydial elementary bodies, thereby compromising the outer protective shell of the EBs and allowing protease penetration. Suitable disulfide reducing agents include, but are not limited to, dithiothreitol, succimer, glutathione, DL-penicillamine, D-penicillamine disulfide, 2,2'-dimercaptoadipic acid, 2,3-dimercapto-1-propone-sulfide acid. Appropriate concentrations of these reducing agents can be readily determined by the skilled artisan without undue experimentation using a 10 $\mu$M concentration of dithiothreitol (the preferred reducing agent) as a guideline. Failure to include a reducing agent in the initial step may prevent DNA of EBs from being isolated in the subsequent step. Dithiothreitol is most effective at opening EBs for protease digestion.

Once the outer shell of the EBs has been released, the pre-incubated material is subjected to protein digestion using a protease (e.g., proteinase K), or functionally equivalent enzyme. The DNA is extracted and subjected to a nucleic acid amplification technique, e.g., PCR. The entire gene or portion thereof containing unique antigenic determinant(s) encoding MOMP or other suitable gene can then be amplified using appropriate primers flanking the gene to be amplified. For example, the gene or portion thereof can be the gene encoding MOMP, OMP-B, GRO-ES, GRO-EL, DNAK, 16S RNA, 23S RNA, the gene encoding a 76 kd attachment protein or a KDO-transferase gene. In an alternative method, guanidine thiocyanate, at preferably a concentration of 4M, or functionally equivalent reducing denaturant may be substituted for the disulfide reduction/protease steps.

The amplified DNA is then separated and identified by standard electrophoretic techniques. DNA bands are identified using ethidium bromide staining and UV light detection. PCR primers can be designed to selectively amplify DNA encoding MOMP of a particular Chlamydia species, such as the MOMP of *C. pneumoniae, C. pecorum, C. trachomatis, C. psittaci*. Primers that are from about 15-mer to about 40-mer can be designed for this purpose.

Antichlamydial Therapy Directed Toward the Initial Stage of Chlamydia Infection A number of effective agents that are specifically directed toward the initial phase of chlamydial infection (i.e., transition of the chlamydial EB to an RB) have been identified. This growth phase, unlike that of the replicating chlamydial microorganism, which uses host cell energy, involves electrons and electron transfer proteins, as well as nitroreductases. Based upon this, it has been shown that the initial phase of Chlamydia infection is susceptible to the antimicrobial effects of nitroimidazoles, nitrofurans and other agents directed against anaerobic metabolism in bacteria.

Nitroimidazoles and nitrofurans are synthetic antimicrobial agents that are grouped together because both are nitro ($NO_2$—) containing ringed structures and have similar antimicrobial effects. These effects require degradation of the agent within the microbial cell such that electrophilic radicals are formed. These reactive electophilic intermediates then damage nucleophilic protein sites including ribosomes, DNA and RNA. Nitroimidazoles and nitrofurans currently are not considered to possess antimicrobial activity against members of the Chlamydia species. This lack of antimicrobial activity, however, is due to the fact that conventional susceptibility testing methods only test for effect on the replicating form of Chlamydia species.

Examples of suitable nitroimidazoles include, but are not limited to, metronidazole, tinidazole, bamnidazole, benznidazole, flunidazole, ipronidazole, misonidazole, moxnidazole, ronidazole, sulnidazole, and their metabolites, analogs and derivatives thereof. Metronidazole is most preferred. Examples of nitrofurans that can be used include, but are not limited to, nitrofurantoin, nitrofurazone, nifurtimox, nifuratel, nifuradene, nifurdazil, nifurpirinol, nifuratrone, furazolidone, and their metabolites, analogs and derivatives thereof. Nitrofurantoin is preferred within the class of nitrofurans.

Throughout this application and for purposes of this invention, "metabolites" are intended to embrace products of cellular metabolism of a drug in the host (e.g., human or animal) including, but not limited to, the activated forms of prodrugs. The terms "analogs" and "derivatives" are intended to embrace isomers, optically active compounds and any chemical or physical modification of an agent, such that the modification results in an agent having similar or increased, but not significantly decreased, effectiveness against Chlamydia, compared to the effectiveness of the parent agent from which the analog or derivative is obtained. This comparison can be ascertained using the susceptability tests described in U.S. patent application Ser. No. 08/911,593 and U.S. patent application Ser. No. 09/025,176 entitled "Methods for In Vitro and In Vivo Susceptability Testing of Chlamydia Species" by Charles W. Stratton and William M. Mitchell, filed Feb. 18, 1998; the entire teachings of which are incorporated herein by reference.

Cells or animals to be treated can already be cryptically infected or they can be subjected to stringent metabolic conditions which cause or induce the replicating phase to enter the cryptic phase. Such stringent conditions can include changing environmental/culturing conditions in the instance where the infected cells are exposed to gamma-interferon; or by exposing cells to conventional antimicrobial agents (such as macrolides and tetracyclines) which induce this cryptic phase of chlamydial infection in human host cells.

Novel Antichlamydial Therapy Directed Toward the Replicating Phase of Chlamydia Infection A unique class of antichlamydial agents that is effective against the replicating phase of Chlamydia (and possibly against some stages of the cryptic stage) have been identified using the susceptibility tests described herein. This novel class of agents comprises ethambutol and isonicotinic acid congeners which include isoniazid (INH), isonicotinic acid (also known as niacin), nicotinic acid, pyrazinamide, ethionamide, and aconiazide; where INH is most preferred. Although these are currently considered effective only for mycobacterial infections, due in part to currently available susceptibility testing methodologies, it has been discovered that these agents in combination with other antibiotics are particularly effective against Chlamydia. It is believed that the isonicotinic acid congeners target the constitutive production of catalase and peroxidase, which is a characteristic of microorganisms, such as mycobacteria, that infect monocytes and macrophages. Chlamydia can also successfully infect monocytes and macrophages.

Using INH to eradicate Chlamydia from macrophages and monocytes subsequently assists these cells in their role of fighting infection. However, these agents appear to be less effective, in vitro, against the cryptic phase. Thus, ethambutol, INH and other isonicotinic acid congeners ideally should be used in combination with agents that target other phases of the chlamydial life cycle. These isonicotinic acid congeners are nevertheless excellent agents for the long term therapy of chronic/systemic chlamydial infection generally, and in particular to chlamydial infection of endothelial and smooth muscle cells in human blood vessels.

Therapy Directed Toward Elementary Bodies of Chlamydia

As discussed above, it has been discovered that adverse conditions, such as limited nutrients, antimicrobial agents, and the host immune response, produce a stringent response in Chlamydia. Such adverse conditions are known to induce stringent responses in other microorganisms (C. W. Stratton, In: *Antibiotics in Laboratory Medicine*, Fourth Edition. Lorian V (ed) Williams & Wilkins, Baltimore, pp 579–603 (1996)) and not surprisingly induce a stringent response in Chlamydia. This stringent response in Chlamydia alters the morphological state of the intracellular microorganism and creates a dormant form, the intracellular EB, which then can cryptically persist until its developmental cycle is reactivated. Conversely, the host cell may lyse and allow the EBs to reach the extracellular milieu. Thus, it is necessary to utilize a combination of agents directed toward the various life stages of Chlamydia and, in particular, against the elementary body for successful management of infection.

During the unique chlamydial life cycle, it is known that metabolically-inactive spore-like EBs are released into the extracellular milieu. Although these released EBs are infectious, they may not immediately infect nearby susceptible host cells until appropriate conditions for EB infectivity are present. The result of this delay in infection is the extracellular accumulation of metabolically-inactive, yet infectious, EBs. This produces a second type of chlamydial persistance referred to herein as EB "tissue/blood load". This term is similar in concept to HIV load and is defined herein as the number of infectious EBs that reside in the extracellular milieu. Direct microscopic visualization techniques, tissue cell cultures, and polymerase chain reaction test methods have demonstrated that infectious EBs are frequently found in the blood of apparently healthy humans and animals. This phenomenon is clearly of great clinical importance in chlamydial infections as these metabolically-inactive EBs escape the action of current antichlamydial therapy which is directed only against the replicating intracellular forms of Chlamydia. The presence of infectious extracellular EBs after the completion of short term, anti-replicating phase therapy for chlamydial infections has been shown to result in infection relapse. Thus, the duration and nature of antichlamydial therapy required for management of chlamydial infections is, in part, dictated by the extracellular load of EBs.

As described in previous sections, it is also believed that persistence of chlamydial infections, in part, may be due to the presence of the cryptic form of Chlamydia within the cells. This cryptic intracellular chlamydial form apparently can be activated by certain host factors, including stress-induced hormones such as cortisone (Yang et al., Infection and Immunity, 39:655–658 (1983); and Malinverni et al., *The Journal of Infectious Diseases,* 172:593–594 (1995)). Antichlamydial therapy for chronic Chlamydia infections must be continued until any intracellular EBs or other intracellular cryptic forms have been activated and extracellular EBs have infected host cells. This reactivation/reinfection by chlamydial EBs clearly is undesirable as it prolongs the therapy of chlamydial infections, as well as increases the opportunity for antimicrobial resistance to occur.

Physiochemical agents have been identified that can inactivate chlamydial EBs in their respective hosts by reducing disulfide bonds which maintain the integrity of the outer membrane proteins of the EBs. For Chlamydia, disruption of the outer membrane proteins of EBs thereby initiates the transition of the EB form to the RB form. When this occurs in the acellular milieu where there is no available energy source, the nascent RB perishes or falls victim to the immune system. Thus, disulfide reducing agents that can interfere with this process are suitable as compounds for eliminating EBs.

One such class of disulfide reducing agents are thioldisulfide exchange agents. Examples of these include, but are not limited to, 2,3-dimercaptosuccinic acid (DMSA; also referred to herein as "succimer"); 3-mercapto-D-vacium (also known as penicillamine); β-lactams (e.g., penicillins, penicillin G, ampicillin and amoxicillin, which produce penicillamine as a degradation product), dithiotreitol, mercaptoethylamine, N-acetylcysteine and glutathione. A particularly effective extracellular antichlamydial agent within this class is meso 2,3-dimercaptosuccinic acid (DMSA), also referred to as succimer, which is a chelating agent having four ionizable hydrogens and two highly charged carboxyl groups which prevent its relative passage through human cell membranes. DMSA thus remains in the extracellular fluid where it can readily encounter extracellular EBs. The two thiol (sulfhydryl) groups on the succimer molecule (DMSA) are able to reduce disulfide bonds in the MOMP of EBs located in the extracellular milieu.

Penicillamine can also be used as a disulfide reducing agent to eliminate chlamydial EBs. However, the use of penicillamine may cause undesirable side effects. Thus, as an alternative, those β-lactam agents which are metabolized or otherwise converted to penicillamine-like agents in vivo (i.e., these agents possess a reducing group) can be orally administered to the animal as a means of providing a controlled release of penicillamine derivatives, by acid hydrolysis of the penicillin, under physiologic conditions. The in vivo production of penicillamine from the degradation of penicillins undoubtedly accounts for the known in vitro ability of penicillins to reduce or prevent the development of infectious chlamydial EBs in cell cultures.

Currently Recognized Agents Active Against Chlamydia Replication

As chlamydial RBs transform into EBs, they begin to utilize active transcription of chlamydial DNA and translation of the resulting mRNA. As such, these forms of Chlamydia are susceptible to currently used antimicrobial agents. The antichlamydial effectiveness of these agents can be significantly improved by using them in combination with other agents directed at different stages of Chlamydia life cycle, as discussed herein.

Classes of suitable antimicrobial agents include, but are not limited to, rifamycins (also known as ansamacrolides), quinolones, fluoroquinolones, chloramphenicol, sulfonamides/sulfides, azalides, cycloserine, macrolides and tetracyclines. Examples of these agents which are members of these classes, as well as those which are preferred, are illustrated below in Table 1.

TABLE 1

Agents Effective Against the Replicating Phase of Chlamydia

| Drug Class | Examples | Preferred |
|---|---|---|
| Quinolones/ Fluoroquinolones | Ofloxacin<br>Levofloxacin<br>Trovafloxacin<br>Sparfloxacin<br>Norfloxacin<br>Lomefloxacin<br>Cinoxacin<br>Enoxacin<br>Nalidixic Acid<br>Fleroxacin<br>Ciprofloxacin | Levofloxacin |
| Sulfonamides | Sulfamethoxazole | Sulfamethoxazole/ Trimethoprim |
| Azalides | Azithromycin | Azithromycin |
| Macrolides | Erythromycin<br>Clarithromycin | Clarithromycin |
| Lincosamides | Lincomycin<br>Clindamycin | |
| Tetracyclines | Tetracycline<br>Doxycycline<br>Minocycline<br>Methacycline<br>Oxytetracyline | Minocycline |
| Rifamycins (Ansamacrolides) | Rifampin<br>Rifabutin | Rifampin |

All members of the Chlamydia species, including *C. pneumoniae*, are considered to be inhibited, and some killed, by the use of a single agent selected from currently used antimicrobial agents such as those described above. However, the inventors have found that complete eradication of Chlamydia cannot be achieved by the use of any one of these agents alone because none are efficacious against all phases of the Chlamydia life cycle and appear to induce a stringent response in Chlamydia causing the replicating phase to transform into cryptic forms. This results in a persistent infection in vivo or in vitro that can be demonstrated by PCR techniques which assess the presence or absence of chlamydial DNA. Nevertheless, one or more of these currently used agents or a new agent directed against the replicating phase of Chlamydia should be included as one of the chlamydial agents in a combination therapy in order to slow or halt the transition of the EB to the RB, as well as to inhibit chlamydial replication.

Maintaining Chlamydia-free Organisms

Because Chlamydia is highly infectious, organisms which have been cleared of extracellular, replicating and cryptic infections must be protected from exposure to viable EBs if the organisms are to remain clear. The inventors have discovered that many of the nutrients and other materials used to maintain continuous cell lines are contaminated with viable Chlamydia EBs. For example, every lot of fetal calf serum has tested positive for the Chlamydia MOMP gene by PCR. Since extensive digestion is required for isolation of the DNA, we have concluded it is bound in EBs. *C. pneumoniae* can also be cultured directly from fetal calf serum. Thus, it is necessary to inactivate EBs in these materials, such as culture media and nutrients, used to maintain the Chlamydia-free status of the organism. Collectively these materials are referred to herein as “maintenance materials”. In one embodiment, nutrients and culture media are subjected to gamma irradiation to inactivate Chlamydia therein. Preferably, the material should be irradiated for a period of time sufficient to expose the material to at least 10,000 rads of gamma radiation. It is important for the material to be contained in vessels that do not absorb high energy radiation. The preferred vessel is plastic. In another embodiment, the maintenance materials are treated with a disulfide reducing agent (e.g., dithiothreitol (10 $\mu$M) for about 30 minutes) and then the treated maintenance materials are passed through a standard submicron (e.g., about 0.45 microns) filtration system. The reducing agent causes any EBs to expand to the size where a 0.45 micron filter will block their passage. Examples of suitable disulfide reducing agents include, but are not limited to, dithiothreitol, succimer, glutathione, DL-penicillamine, D-penicillamine disulfide, 2,2'-dimercaptoadipic acid, 2,3-dimercapto-1-propone-sulfide acid. In yet another embodiment, maintenance materials are treated with a disulfide reducing agent, preferably dithiothreitol (e.g., about 10 $\mu$M concentration), before the materials are passed through a filtration system to remove Chlamydia therefrom.

In order to insure that research tools, such as cell lines and animals, remain Chlamydia-free, an assay has been designed to evaluate whether an organism is Chlamydia-free. The method comprises obtaining a sample of cells or tissue culture; culturing the cells in the absence of cycloheximide and determining the presence or absence of Chlamydia nucleic acid by a suitable amplification technique, such as PCR. The absence of nucleic acid amplification signal is indicative that the status of the organism is Chlamydia-free. Detailed assays for such evaluation are described in U.S. patent application Ser. No. 08/911,593; U.S. patent application Ser. No. 09/025,521, entitled “Diagnosis and Management of Infection Caused by Chlamydia”, filed Feb. 18, 1998; U.S. patent application Ser. No. 09/025,596 “Identification of Antigenic Peptide Sequences”, filed Ser. No. 09/025,176 and U.S. patent application Ser. No. 09/025,521 entitled “Methods for In Vitro and In Vivo Susceptibility Testing”, filed Feb. 18, 1998; the entire teachings of which are incorporated herein by reference.

Diagnostic Reagents

The invention also provides a diagnostic reagent pack or kit comprising one or more containers filled with one or more of the ingredients used in the assays of the invention. Optionally, associated with such container(s) can be a notice in the form prescribed by a governmental agency regulating the manufacture, use or sale of diagnostic products, which notice reflects approval by the agency of manufacture, use of sale for human administration. The pack or kit can be labeled with information regarding mode of administration, sequence of execution (e.g., separately, sequentially or concurrently), or the like. The pack or kit can be a single unit assay or it can be a plurality of unit assays. In particular, the agents can be separated, mixed together in any combination, present in a single vial or tablet. For the purpose of this invention, unit assay is intended to mean materials sufficient to perform only a single assay.

Equivalents

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

We claim:

1. A method for clearing biological material of Chlamydia, comprising the step of contacting the biological material with at least two agents, each of which is effective against a different phase of chlamydial life cycle, until the biological material is negative for Chlamydia according to a test that detects elementary body phase Chlamydia, replicating phase Chlamydia, and cryptic phase Chlamydia.

2. The method according to claim 1 wherein the agents are selected from the group consisting of:

a) agents effective against cryptic phase of chlamydial life cycle;

b) agents effective against elementary body phase of chlamydial life cycle; and c) agents effective against replicating phase of chlamydial life cycle.

3. The method according to claim 2 wherein the agent effective against the elementary body phase is a disulfide reducing agent.

4. The method according to claim 2 wherein the agent effective against the cryptic phase is a nitroaromatic compound.

5. The method according to claim 4, wherein the nitroaromatic compound is selected from the group consisting of nitroimidazoles, nitrofurans, analogs, derivatives and combinations thereof.

6. The method according to claim 1, wherein the test that detects elementary body phase Chlamydia, replicating phase Chlamydia, and cryptic phase Chlamydia comprises a step of nucleic acid amplification.

7. The method of claim 1, wherein said test comprises the steps of:

(a) providing a sample of said biological material contacted with said agents;

(b) contacting said sample with a disulfide reducing agent;

(c) contacting said disulfide reducing agent-contacted sample with a protease;

(d) extracting DNA from said protease-contacted sample;

(e) amplifying from said extracted DNA a chlamydial gene or portion thereof, if present, by polymerase chain reaction; and (f) determining the presence or absence of said amplified chlamydial gene or portion thereof.

8. The method according to claim 3, wherein said disulfide reducing agent is selected from the group consisting of 2,3-dimercaptosuccinic acid, penicillamine, β-lactams, dithiotreitol, mercaptoethylamine, and N-acetylcysteine.

9. The method according to claim 8 wherein said disulfide reducing agent is penicillamine.

10. The method according to claim 8, wherein the β-lactam is amoxicillin.

11. The method according to claim 1, wherein the biological material is a cell line or a non-human animal.

12. The method according to claim 1, wherein one of the agents is selected from the group consisting of macrolide antibiotics and azalide antibiotics.

13. The method according to claim 1, wherein one of the agents is a rifamycin.

14. A method for obtaining a Chlamydia-free cell line or animal and maintaining the cell line or animal free from Chlamydia infection, comprising the steps of:

(a) contacting the cell line or animal with at least two agents, each of which is effective against a different phase of chlamydial life cycles until the biological material is negative for Chlamydia according to a test that detects elementary body phase Chlamydia, replicating phase Chlamydia, cryptic phase Chlamydia;

(b) providing to the cell line or animal obtained in step (a) a source of nutrients that have been treated to remove or inactivate any Chlamydial elementary bodies therefrom; and (c) optionally, contacting the Chlamydia-free cell line or animal with agents that are effective against Chlamydia.

15. The method of claim 14 wherein the agents are selected from the group consisting of:

a) agents effective against cryptic phase of chlamydial life cycle;

b) agents effective against elementary body phase of chlamydial life cycle; and c) agents effective against replicating phase of chlamydial life cycle.

16. The method according to claim 14, wherein the biological material is a non-human animal.

17. A kit comprising (a) first agent which is effective against a first phase of Chlamydial life cycle;

(b) second agent which is effective against a second phase of Chlamydial life cycle; and (c) means for performing a test that detects elementary body phase Chlamydia, replicating phase Chlamydia, and cryptic phase Chlamydia.

18. The kit according to claim 17, said kit further comprising a source of nutrients that have been treated to remove or inactivate any Chlamydial elementary bodies therefrom.

19. The kit according to claim 17, wherein one of said first agent and said second agent is a disulfide reducing agent.

20. The kit according to claim 19, wherein said disulfide reducing agent is selected from the group consisting of 2,3-dimercaptosuccinic acid, penicillamine, β-lactams, dithiotreitol, mercaptoethylamine, and N-acetylcysteine.

21. The kit according to claim 20 wherein the disulfide reducing agent is penicillamine.

22. The kit according to claim 20 wherein the β-lactam is amoxicillin.

23. The kit according to claim 17, said kit further comprising a cell line.

24. The kit according to claim 23, wherein said cell line is selected from the group consisting of HeLa, HL, H-292, HuEVEC, Hep2, African green monkey cell, and McCoy cell lines.

* * * * *